United States Patent [19]

Langdon

[11] Patent Number: 4,865,821
[45] Date of Patent: Sep. 12, 1989

[54] INSTRUMENT STERILIZATION RACK

[76] Inventor: Robert S. Langdon, 29 Beaver La., Bedford, N.H. 03102

[21] Appl. No.: 223,918

[22] Filed: Jul. 25, 1988

[51] Int. Cl.⁴ .......................... A61L 2/06; A61L 2/26
[52] U.S. Cl. .................................... 422/300; 422/104; 422/297; 206/370; 206/557; 211/168; 211/181
[58] Field of Search ............... 422/104, 297, 300, 310; 206/363, 370, 557; 34/239, 240; 211/13, 168, 181

[56] References Cited

U.S. PATENT DOCUMENTS

| | | | |
|---|---|---|---|
| 3,925,014 | 12/1975 | Langdon | 422/300 |
| 4,229,420 | 10/1980 | Smith et al. | 422/104 |
| 4,342,391 | 9/1982 | Schainholz | 422/310 |
| 4,512,466 | 4/1985 | Delang | 206/370 |
| 4,577,755 | 3/1986 | Ramsay | 206/370 |

Primary Examiner—David L. Lacey
Assistant Examiner—Gregory Muir
Attorney, Agent, or Firm—Chilton, Alix & Van Kirk

[57] ABSTRACT

A surgical instrument rack for storing and supporting pivoted surgical instruments is defined by an open frame-type structure. The instruments are retained to the rack by a lock bar which also functions to maintain a pivotal frame in a position forcing the instruments to an open condition for cleaning and sterilization. Separator clips separate the instruments into groupings. A removable retainer clip snaps over the instruments and is adapted to display indicia referencing instruments in each grouping to facilitate return of the instruments to the rack after usage.

3 Claims, 3 Drawing Sheets

INSTRUMENT STERILIZATION RACK

BACKGROUND OF THE INVENTION

1. FIELD OF THE INVENTION

The present invention relates generally to devices for handling surgical instruments and the like and in particular to devices for maintaining the instruments in a sterilized condition, devices for presenting the instruments at the time of use in an organized manner and devices for facilitating cleaning and sterilization of the instruments after use. More specifically, this invention relates to a surgical instrument rack for receiving and properly orienting instruments during sterilization and storage and also for organizing groups of instruments in a pre-established arrangement for use by operating personnel.

2. DESCRIPTION OF THE PRIOR ART

In the interest of facilitating and standardizing operating room procedures, it is common practice to group surgical instruments into standard or basic sets. The organization of the instrument sets is determined by the surgical procedure to be followed. The standard groups of instruments are stored in a sterilized condition until usage. Subsequent to usage, the instruments are subject to a multi-step cleaning and sterilization procedure. The cleaning may include immersion in an ultrasonic bath to remove all foreign matter. It is important that all of the instruments are thoroughly cleaned prior to the sterilization process. After cleaning, the instruments are assembled into a basic set. The set may be arranged in a perforated or a wire mesh bottom tray for sterilization. During preliminary cleaning and sterilization, all hinged, pivoted or jointed instruments must be opened or unlocked to permit contact of the steam or sterilization fluids with all of the instrument surfaces.

The surgical instruments are typically removed from a tray in the operating room, arranged on a stand and organized in a fashion which permits the instruments to be handed to the surgeon, as needed, in a very efficient manner. The arrangement of numerous instruments in loose fashion on a Mayo stand presents the potential for external droppage, thus necessitating emergency sterilization. The numerous manipulative steps required between the use of an instrument also presents a potential that an instrument may be inadvertently misplaced and will thus not be easily located when needed.

A number of devices have been advanced for minimizing the handling of surgical instruments, as well as organizing the surgical instruments for use by the surgeon. In U.S. Pat. No. 3,925,014 of the inventor of the present invention, a rack for storing and supporting sterile hinged instruments comprises an open framework for supporting the instruments in side-by-side relationship. The rack includes a pair of removable retaining bars and is particularly well suited for use with pivoted or hinged surgical instruments. The basic sets of the hinged surgical instruments remain in the rack except when used by the surgeon. The rack is employed to properly orient the instruments during the cleaning and subsequent sterilization of the instruments and to retain and position the instruments in the unlocked and open condition. One retaining bar holds the instruments in the open condition during the cleaning and sterilization. A second bar secures the instruments to the rack until use regardless of the position of the rack and is ordinarily only removed in the operating room.

SUMMARY OF THE INVENTION

Briefly stated, the invention in a preferred form is a new and improved instrument sterilization rack having particular applicability in connection with pivoted surgical instruments for retaining the instruments in proper position for cleaning and sterilization and for organizing the instruments for use by the surgeon.

The rack comprises a support frame formed from a generally continuous tubular frame bar which forms parallel front and rear bases and connecting side members. The members each integrally extend generally upwardly, rearwardly, and downwardly to integrally connect between the laterally opposed end portions of the front and rear bases. A support bar extends laterally between the side members and is vertically offset from the bases and parallel thereto.

A retractable instrument positioner is pivotally mounted to the support frame at an upper rear location. The retractable positioner comprises a continuous bar forming parallel linear second and third support bars. The second support bar defines the pivotal axis of the positioner. The second support bar extends laterally beyond opposing lateral portions of the support bases to ensure that the end instruments do not accidentally fall off the rack. The second and third bars define a fixed plane for supporting the underside of the surgical instruments in side-by-side relationship. The third bar is pivotally positionable at an open position to engage respective handle portions of the instruments to vertically displace the handle portions above the support plane whereby an engaged instrument handle will be displaced away from the other cooperative handle of each engaged pivoted instrument for maintaining the instruments in an open condition during cleaning and sterilization.

A plurality of laterally-spaced separator clips are mounted to the support frame and are laterally slidable therealong. Each of the separator clips has a rounded socket for closely engaging the first support bar, a rounded socket for closely engaging the rear support base at the underside thereof and an intermediate rounded vertex which is vertically offset from the rear support base.

A removable lock bar is insertable through the vertices for close reception by the separator clips from either lateral end of the rack. The lock bar engages a handle portion of the instruments to thereby securably capture the instruments between the second bar and the locking bar. The lock bar laterally extends beyond opposing portions of the support frame and is engagable with the positioner to lock the third bar in the open position. The lock bar preferably has a rounded tapered contour at one end of the bar to facilitate insertion into the rack.

A removable elongated retainer clip is releasably mounted to the side members and laterally extends from the members in vertically offset relationship. The retainer clip includes a display panel adapted to be affixed with indicia for identifying corresponding laterally-spaced instruments which are loaded in the rack.

An object of the invention is to provide a new and improved surgical instrument rack for facilitating cleaning and sterilization of surgical instruments and for organizing the instruments for usage by a surgeon.

Another object of the invention is to provide a new and improved surgical instrument rack having an efficient construction which facilitates cleaning and sterilization of the rack and ensures that the instruments will be retained on the rack until removed for usage.

A further object of the invention is to provide a new and improved surgical instrument rack wherein pivoted surgical instruments may be loaded onto the rack and transformed to an open position for cleaning and sterilization in a very efficient manner.

Other objects and advantages will become apparent from the drawings and the specification.

DETAILED DESCRIPTION OF THE INVENTION

With reference to the drawings wherein like numerals represent like parts throughout the figures, a surgical instrument rack in accordance with the present invention is generally designated by the numeral 10. The rack 10 generally has an open frame configuration. The surgical instrument rack 10 is employed for receiving and retaining a multiplicity of surgical instruments and has particular applicability in connection with dual armed, pivoted surgical instruments such as scissors, forceps, needle holders, retractors, tongs, and the like. One such pivoted surgical instrument is depicted for purposes of illustrating the invention and is designated generally by the numeral 12. As will be further detailed below, the surgical instrument rack 10 functions to receive the surgical instruments, to store the instruments in an efficient and secure manner, to organize the instruments for usage and to maintain the instruments in a pivotally open condition to facilitate cleaning and sterilization of the instruments after usage.

Figure 1:
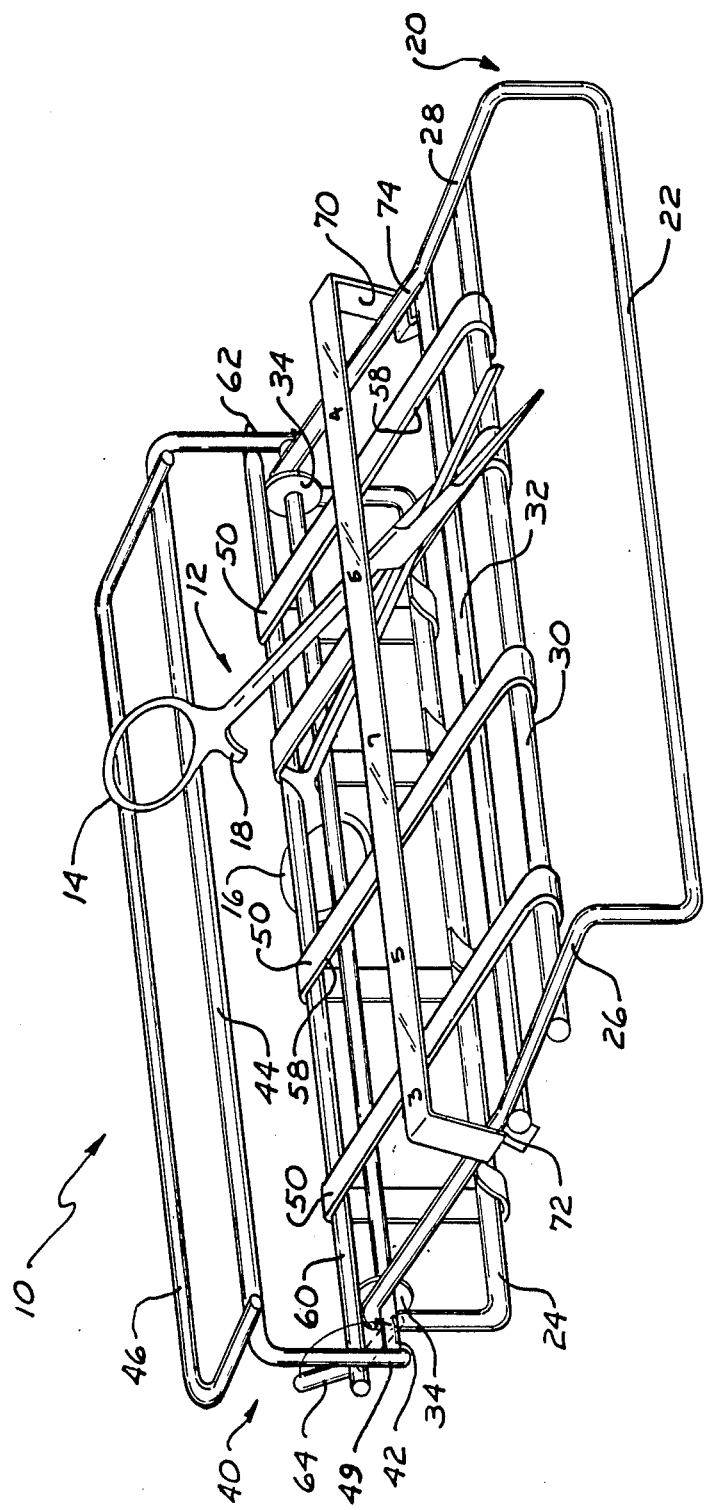
FIG. 1 is a perspective view of a surgical instrument rack in accordance with the present invention depicting a pivoted surgical instrument supported on the rack in a position which facilitates cleaning and sterilization.
Figure 2:
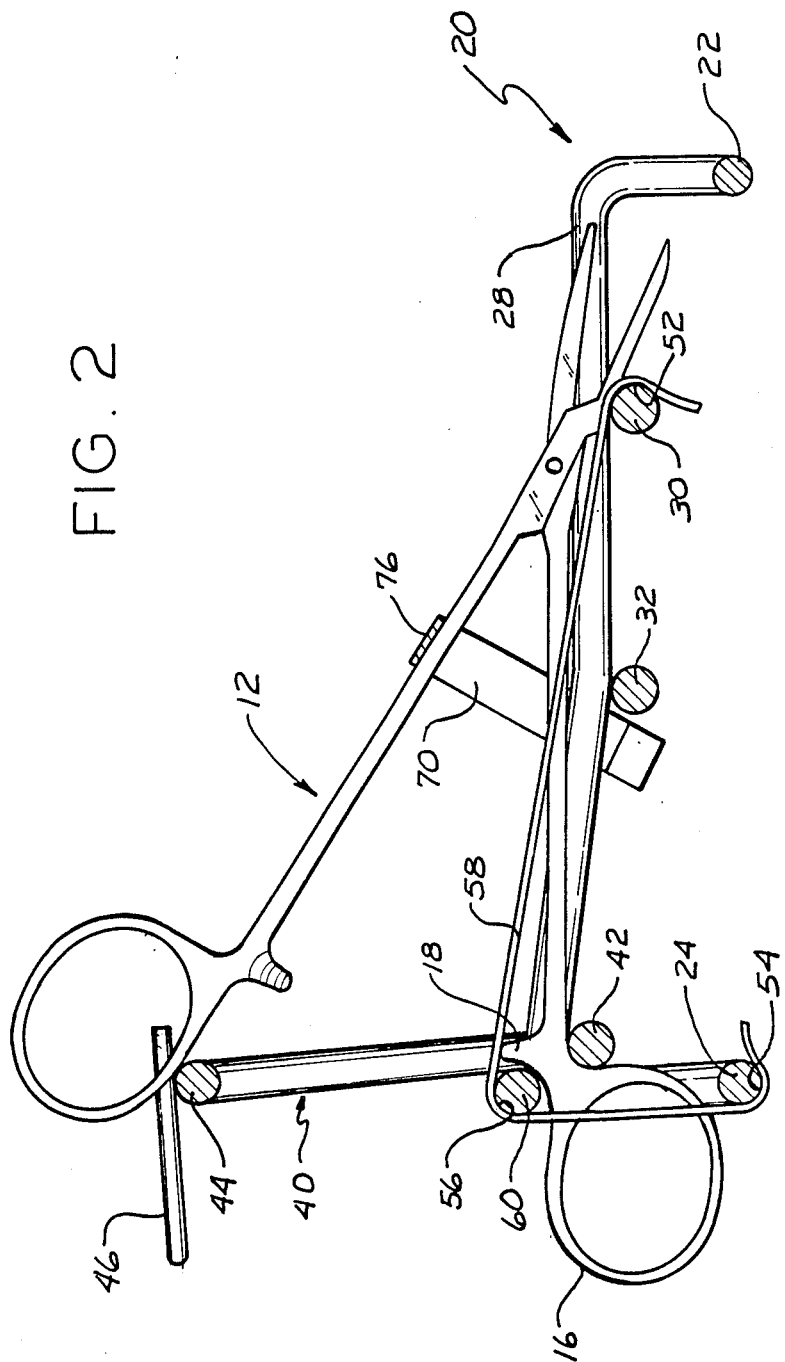
FIG. 2 is a cross-sectional side elevational view of the surgical instrument rack and instrument of FIG. 1.
Figure 3:
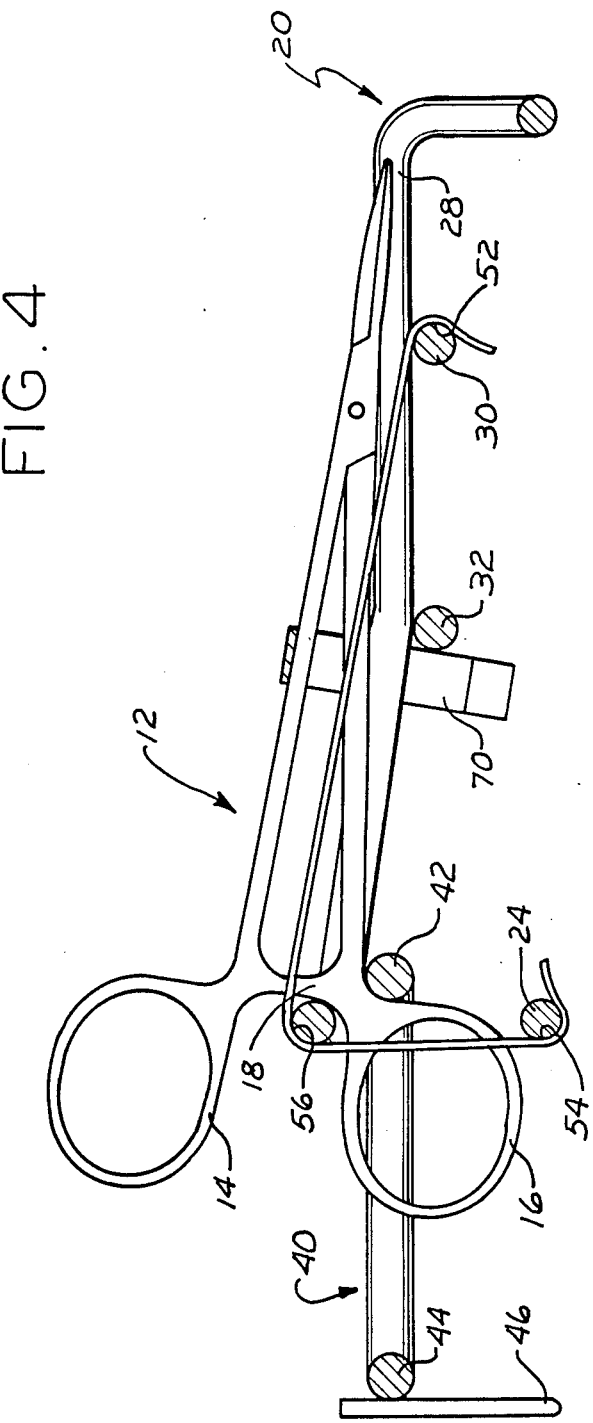
FIG. 3 is a cross-sectional side elevational view of the surgical instrument rack and instrument of FIG. 1 depicting the rack in a retracted position which facilitates withdrawal of an instrument from the rack for usage.

Surgical instrument 12 which is illustrated and described for purposes of explaining and describing the rack 10 is a surgical forceps of conventional form comprising cooperative pivoted arms 14 and 16. Each of the arms has a handle portion and a distal work portion and includes a serrated locking post 18. In the open position, the handle portions and the work portions are spaced apart to expose the instrument surfaces including the surfaces in the vicinity of the pivot joint. It should be appreciated that the rack 10 is adapted for multiple surgical instruments having a wide variety of shapes and dimensions. To accomplish the described multiple functions, the rack 10 is pivotally transformable between an open mode, such as illustrated in FIGS. 1 and 2, for holding pivoted instruments in an open position during sterilization and cleaning and a retracted mode, such as illustrated in FIG. 3, for permitting the instruments to be withdrawn from the rack for usage or loaded onto the rack after usage.

The surgical rack 10 has a support frame 20 which is formed from a rounded bar of stainless steel in a quasi continuous-like fashion. The bar is bent to form a front laterally extending support base 22 and a parallel transversely spaced, rear support base 24. Support base 24 may be a separate element which is welded at opposing ends to form the substantially continuous support frame 20. The bases 22 and 24 rest on a support surface to form the principal support for the rack for both the open and retracted modes. The bar is bent upwardly and angled rearwardly and downwardly to connect between the opposing bases in continuous curvilinear fashion to form side connector segments 26 and 28, respectively, which are slightly inclined upwardly toward the rear base 24. The frame 20 has a relatively low profile to facilitate stacking.

A pair of parallel support bars 30 and 32 extend laterally between the connector segments 26 and 28. The support bars 30 and 32 are welded at end locations to the underside of the connector segments 26 and 28. The front support bar 30 functions as a cross-support for the surgical instruments. Washers 34 or other similar members are welded at the upper rear portion of the connector segments to provide an aperture or pivot yoke for a pivotal connection.

A pivotally retractable positioner frame 40 comprises a linear pivot bar 42 which is received in the apertures defined by the washers 34 for pivotal mounting thereby. Preferably, a stainless steel bar of material is bent to form a quasicontinuous four-sided loop which includes the pivot bar 42 and an instrument positioner bar 44. The positioner bar is parallel and generally opposite the pivot bar 42. The pivot bar 42 defines the pivotal axis of the positioner frame 40. The engagement bar 44 is engagable at the underside of the upper instrument handles 14 for forcing the hinged or pivoted instruments 12 to the open condition when the positioner frame 40 is in the generally upright pivotal position of FIGS. 1 and 2.

A generally U-shaped support leg 46 is welded to opposing laterally-spaced end portions of the engagement bar 44. The support leg 46 rests on a support surface to maintain the positioner frame in the generally horizontal orientation illustrated in FIG. 3 for facilitating removal of the instruments from the rack 10. The spacing between bars 42 and 44 is dimensioned to accommodate reception of the lower instrument handle 16 in the retracted mode as well as to force the handles sufficiently apart to pivotally open the instruments in the open mode. It should be noted that both the pivot bar 42 and the engagement bar 44 laterally extend beyond the corresponding connector segments 26 and 28.

A plurality of substantially identical separator clips 50 engage the transverse support bar 30 and the rear support base 24 in a spring-loaded type engagement. The clips 50 are preferably shaped from flattened strips of spring steel into an angle configuration. The clips are configured with spring-type arcuate sockets 52 and 54 (FIGS. 2 and 3) which are suitably spaced to facilitate a snap-type engagement over the support bar 30 and under the rear base 24. The spring-loaded separator clips 50 function to separate the surgical instruments into groups and hence, organize the instruments for a given procedure. The edges 58 of the clips also function as retaining shoulders which engage the end instruments of the groups to ensure that the instruments maintain the upright orientation in the rack. The separator clips 50 are clipped into position and laterally spaced to organize the instruments into pre-established sets. When mounted, each separator clip extends (front to rear) upwardly and downwardly to form an arcuate vertex 56. The aligned vertices 56 of the separator clips define a series of aligned laterally-spaced slots for receiving a lock bar 60.

Figure 4:
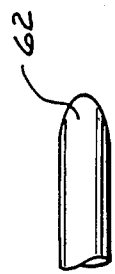
FIG. 4 is an enlarged fragmentary view of a portion of a locking bar of the surgical instrument rack of FIG. 1.

The lock bar 60 is an elongated rod having a length exceeding the lateral width of frames 20 and 40. The bar has a tapered contoured end 62, as best illustrated in FIG. 4. The opposing end of the looking bar includes a handle 64 which extends orthogonally from relative to the lock bar longitudinal axis for securing the bar in the lock position. After the instruments are mounted in the rack, and the positioner frame is pivoted to the open upright position for opening the instruments, as illustrated in FIGS. 1 and 2, the lock bar 60 is inserted trough the slots defined by vertices 56. The contoured end 62 facilitates insertion through the separator clip slots. An end portion of the lock bar extends beyond the positioner frame and interferes with the end side section 49 of the positioner frame to prevent the frame from repivoting to the retracted position of FIG. 3. The lock bar 60 is essentially captured in the rack by the interference-type cooperation of the separator clips 50 and the upper surfaces of instrument handles 16.

Lock bar 60 is a removable bar, which after insertion as previously described, is locked to the rack by rotating the handle in the direction of the arrow of FIG. 1. The handle 64 is thus captured between the end section 49 of the frame 40 and connector section 26. The lock bar extends and is engagable behind the cooperative serrated locking post 18 of the instruments which are mounted to the rack and above one of the hinged arms 16 of each of the instruments. The lock bar 60 and pivot bar 42 cooperate to capture the instrument and hence lock the instrument in position on the rack to thus prevent the instrument from falling off of the rack—even in the event that the rack is inverted or dropped.

When the rack rests on a support surface, under normal circumstances, the lock bar 60 does not contact the instruments or only very lightly contacts the instruments. The lock bar 60 is removed by rotating the handle (opposite the FIG. 1 arrow) and then withdrawing the lock bar laterally toward the left, as illustrated in FIG. 1, when it is desired for usage to withdraw instruments carried by the rack. It should be appreciated that the lock bar may be inserted from either the left end or the right end, as viewed in FIG. 1.

The lock bar 60 may also be inserted and locked in place when the positioner frame 40 is retracted, as illustrated in FIG. 3, to thereby lock the instruments to the rack prior to usage.

An elongated removable retainer clip 70 has a pair of spaced, opposing folded sockets 72 and 74 which are adapted to clip at the underside of the connector segments 26 and 28, respectively. The retainer clip 70 has a loaded spring-clip configuration which upon mounting to the connectors 26 and 28 rearwardly adjacent support bar 32 snaps into position. The clip 70 extends upwardly from the support frame 20 and laterally traverses the support frame in a generally offset vertical orientation. The clip 70 retainably engages intermediate top surfaces of the instruments to form an auxiliary structure for securing the instruments to the rack. The retainer clip 70 is removable from the support frame to permit loading or withdrawal of the instruments.

An additional function of the retainer clip 70 is to support a readibly visible display panel 76 to display indicia identifying various instruments or numbers of instruments for each of the instrument groupings (defined by the separator clips). For example, as illustrated, if the number of instruments for each grouping is displayed on the indicia clip, the users will know how many instruments should be returned to the rack and instrument loss will be reduced. Thus, the display panel 76 facilitates accurate pre-operative and post-operative instrument counts. Alternatively, indicia which identifies specific instruments may be displayed on panel 76.

The surgical instrument rack 10 in accordance with the present invention is preferably formed from stainless steel materials. The rack 10 is preferably designed and fabricated so that the number of joints and crevices susceptible to accumulation of foreign matter is minimized. Accordingly, rounded stock is preferably used where feasible and the number of weld joints is minimized.

The instruments arranged on the rack 10 ordinarily remain on the rack at all times except when used. After the instruments have been used, the instruments are immediately returned to the rack. After all instruments have been returned to the rack, the positioner fram is pivoted to the upright position to open the instruments. The lock bar 60 is re-inserted as previously described. At the initiation of the cleaning procedure, the positioner bar 44 engages the underside of the instruments to hold the instruments in the open position throughout the cleaning and sterilization procedure. When the instruments are ready for usage, the lock bar is removed from the rack and the instruments may then be relatively easily withdrawn from the rack as needed.

While a preferred embodiment of the forgoing invention has been illustrated for purposes of describing the invention, the foregoing description should not be deemed a limitation of the invention herein. Accordingly, various modification, adaptations, and alternatives may occur to one skilled in the art without departing from the spirit and the scope of the present invention.

What is claimed is:

1. A surgical instrument rack for supporting instruments having handle portions during cleaning and sterilization of said instruments comprising:

support means for supporting a plurality of elongated pivoted instruments in upstanding side-by-side relationship, said support means comprising a generally continuous tubular frame bar forming parallel front and rear support bases and connecting side segments each of said side segments integrally extending generally upwardly, rearwardly and downwardly to integrally connect between laterally opposed portions of said front and rear bases, a first support member extending laterally between said side segments vertically offset from said bases and generally parallel thereto;

retractable positioner means pivotally mounted to said support means comprising generally continuous bar means forming parallel linear second and third support members, said second support member defining the pivotal axis of said positioner means and extending laterally beyond opposing lateral end portions of said support bases, said first and second members defining a fixed plane for supporting the underside of the instruments in side-by-side relationship, said third member being pivotally positionable to an open mode to engage a handle portion of the instruments to vertically displace the handle portion above said support plane whereby an engaged instrument handle portion will be displaced away from the other handle portion of each such engaged pivoted instrument for maintaining the instruments in an open condition during cleaning and sterilization;

clip means comprising a plurality of laterally-spaced clips mounted to said support means and laterally slidable therealong, each said clip having a first rounded socket for closely engaging said first support member, a second rounded socket for closely engaging said rear support base at the underside thereof, and an intermediate rounded vertex generally vertically offset from said rear support base;

a removable lock bar insertable from either lateral end thereof for close reception by said clips along said vert-ices so that said lock bar engages a handle portion of said instruments to thereby capture said instruments between said second member and said lock bar, said lock bar being positioned so as to laterally extending beyond opposing portions of said support means and engagable with said positioner means to lock said third member in the open mode; and retainer clip means releasably mounted to said side segments and laterally extending from said segments in vertically offset relationship, for retaining instruments to said support means and positioner means, said retainer clip means comprising a display panel affixed with indicia.

2. The surgical instrument rack of claim 1 wherein the lock bar has a rounded tapered contour at one end thereof.

3. The surgical instrument rack of claim 1 wherein the positioner means further comprises a rest member extending generally perpendicular to the plane defined by said second and third support members, said positioner means being pivotally retractable to a position wherein when the rest member and support means rest on a common planar support surface, said second and third support members define a generally horizontal plane.

* * * * *